United States Patent [19]

Lal

[11] Patent Number: 5,378,805
[45] Date of Patent: Jan. 3, 1995

[54] IMMUNOREACTIVE HTLV-I/II ENV AND POL PEPTIDES

[75] Inventor: Renu B. Lal, Atlanta, Ga.

[73] Assignee: United States of America, Washington, D.C.

[21] Appl. No.: 574,352

[22] Filed: Aug. 29, 1990

[51] Int. Cl.$^6$ ............................................. C07K 7/08
[52] U.S. Cl. .................................. 530/326; 930/10; 930/220; 424/187.1; 530/826
[58] Field of Search ............... 424/89; 530/324, 325, 530/326, 826; 430/10, 220

[56] References Cited

U.S. PATENT DOCUMENTS

| | | | |
|---|---|---|---|
| 4,804,746 | 2/1989 | Yoshida et al. | 530/327 |
| 4,833,071 | 5/1989 | Wang et al. | 435/5 |
| 5,017,687 | 5/1991 | Vahlne et al. | 424/89 |
| 5,066,579 | 11/1991 | Reyes | 530/324 |
| 5,254,457 | 10/1993 | Minassian et al. | 530/388.35 |
| 5,260,189 | 11/1993 | Formoso et al. | 530/326 |

FOREIGN PATENT DOCUMENTS

WO90/08162 7/1990 WIPO.

OTHER PUBLICATIONS

*Science*, Helen Lee, "High Rate of HTLV-II . . . ", vol. 244, pp. 471-475, Apr., 1989.
*Journal of Infectious Diseases*, Renu Lal, "Serologic Discrimination . . . ", vol. 163 pp. 41-46, 1991 (Jan.)
*Journal of Virology*, Renu Lal, "Characterization of Immunodominant . . . ", vol. 65, No. 4, pp. 1870-1876, Apr. 1991.
*Journal of Infectious Diseases*, J. J. Lipka, "Determination of a Unique . . . ", pp. 353-357, Aug. 1990, vol. 162.
*Human Retrovirology*, Peter Horal, "Epitope Profiles of HTLV-I . . . ", pp. 461-467, 1990.
*The Lancet*, Chen, "Type-Specific Antigens . . . ", vol. 336, pp. 1153-1155, 1990.
*Blood*, Anderson et al., "Serological Confirmation of . . . ", vol. 74, pp. 2585-2591, Nov. 1989.
*Journal of Immunology*, T. Copeland et al., "Envelope Proteins of Human . . . ", vol. 137, pp. 2945-2951, No. 9, Nov. 1986.
Reeck et al, "'Homology' in Proteins . . . ", *Cell 50*:667, (Aug. 1987).
*Biological Abstracts/RRM* 39(5): MT-91, Fef Nos. 52821 and 52866, Sep. 8, 1990.
Kuroda et al., *Int. J. Cancer*, 45: 865-868, May 15, 1990.
Sodroski et al., *Science* 225:421-424, 27 Jul. 1984.
Kurata et al., *J. of Immunology* 143:2024-2030, Sep. 15, 1989.
Palker et al., J. of Immunology 136:2393-2397, Apr. 1, 1986.
Palker et al., J. of Immunology 142:971-978, Feb. 1, 1989.

*Primary Examiner*—Stephen G. Walsh
*Attorney, Agent, or Firm*—Needle & Rosenberg

[57] ABSTRACT

The present invention relates a peptide having specific immunoreactivity to antibodies to HTLV-I, HTLV-II, or combinations thereof comprising a peptide selected from the group consisting of:
  Env-1 (HTLV-I; a.a 191-214)LPHSNLDHILEP-SIPWKSKLLTLV,
  Env-2 (HTLV-II; a.a 187-210)VHDSD-LEHVLTPSTSWTTKILKFI,
  Env-5 (HTLV-I; a.a 242-257)SPNVSVPSSSSTPLLY,
  Gag-1a (HTLV-I; a.a 102-117)PPSSPTHDPPDSD-PQI,
  Pol-3 (HTLV-I; a.a 487-502)-KQILSQRSFPLPPPHK, and analogues thereof, wherein the amino acids in the sequence may be substituted as long as the immunoreactivity to antibodies to HTLV-I or HTLV-II derived from the three dimensional conformation of the sequences is substantially preserved.

The invention is further directed to an immunoassay method for the detection of antibodies to HTLV-I, HTLV-II or a combination thereof, a test kit for the detection of said antibodies, a peptide composition containing said peptides and a vaccine.

2 Claims, 5 Drawing Sheets

IMMUNOREACTIVE HTLV-I/II ENV AND POL PEPTIDES

BACKGROUND OF THE INVENTION

1. Field of the Invention

The present invention relates to peptides derived from structural gene products of HTLV-I and HTLV-II selected from the group consisting of Env-1 (HTLV-I; a.a. 191–214), Env-2 (HTLV-II; a.a. 187–210), Env-5 (HTLV-I; a.a. 242–257); Gag-1a (HTLV-I; a.a. 102–117) and Pol-3 (HTLV-I; a.a. 487–502), and immunoassays, test kits and vaccines using these peptides.

2. Discussion of Related Art

Human T-cell lymphotropic viruses (HTLV) types I and II are closely related human retroviruses (Wachsman W, Golde DW, Chen ISY. HTLV and human leukemia: Perspectives. Semin Hematol 1986;23:246–56). HTLV-I is etiologically associated with adult T-cell leukemia (ATL) and with a chronic neurologic disorder known as HTLV-I-associated myelopathy/tropical spastic paraparesis (HAM/TSP; (Ehrlich GD, Poiesz BJ. Clinical and molecular parameters of HTLV-I infection. Clin Lab Med 1988;8:65–84). In contrast, HTLV-II, which was first isolated from a patient with a variant of hairy cell leukemia (Kalyanaraman VS, Sarngadharan MG, Robert-Guroff M, et al. A new subtype of human T-cell leukemia virus (HTLV-II) associated with a T-cell variant of hairy cell leukemia. Science 1982;218:571-3), has not been associated with any specific disease (Blattner WA. Retroviruses. In: Evans AS, ed. Viral Infections of Humans: Epidemiology and Control, ed 3. New York: Plenum 1989:545– 92). While HTLV-I infection is endemic in southwestern Japan, the Caribbean, and some regions of Africa (Ehrlich GD, Poiesz BJ. Clinical and molecular parameters of HTLV-I infection. Clin Lab Med 1988;8:65–84), HTLV-II has been reported mainly in intravenous drug users (Lee H, Swanson P, Shorty VS, Zack JA, Rosenblalt JD, Chen I. High rate of HTLV-II infection in seropositive IV drug abusers in New Orleans. Science 1989;244:471–5.) Concern about transmission of HTLV-I/II infection from contaminated blood products has been intensified by serologic evidence of HTLV-I in volunteer blood donors (Williams AE, Fang CT, Slamon DJ, et al. Seroprevalence and epidemiological correlation of HTLV-I infection in U.S. blood donors. Science 1988;240:643–6; Anderson DW, Epstein JS, Lee TH, et al. Serologic confirmation of human T-lymphotropic virus type I infection in healthy blood and plasma donors. Blood 1989;74:2585–91), and the U.S. Food and Drug Administration has suggested HTLV-I screening of all donated blood (Public Health Service working group. Licensure of screening tests for antibody to human T-lymphotropic virus type-I. MMWR 1988;37:736–47; Kaplan JE, Khabbaz RF. HTLV-I: Newest addition to blood donor screening. Am Fam Physician 1989;40:189–95). Recent data from the screening of blood donors indicate that more than half of those seropositive for HTLV-I indeed may be infected with HTLV-II (Chen ISY, Rosenblat JD, Black AC, Arrigo SJ, Green PL. 1990. HTLV-II Prevalence and regulation of gene expression. AIDS Res Hum Retroviruses 6:134–5.) In addition, a high percentage of the HTLV seroreactivity among intravenous drug users in the United States may be due to HTLV-II infection (Lee H, Swanson P, Shorty VS, Zack JA, Rosenblalt JD, Chen I. High rate of HTLV-II infection in seropositive IV drug abusers in New Orleans. Science 1989;244:471–5). In the absence of serological assays that can distinguish HTLV-I from HTLV-II infection (Chen ISY, Rosenblat JD, Black AC, Arrigo SJ, Green PL. 1990. HTLV-II Prevalence and regulation of gene expression. AIDS Res Hum Retroviruses 6:134–5), counseling such individuals about HTLV-I associated diseases may be inappropriate.

The overall structural similarity as well as the identity of much of the primary amino acid sequence (Myers G, Josephs SF, Rabson AB, Smith TF, Wong Staal F. In: Human retroviruses and AIDS. Los Alamos National Laboratory, Los Alamos, N.M. 1988) would suggest antigenic cross-reactivity between HTLV-I and HTLV-II, and indeed, none of the serological assays, to date, can reliably distinguish between these two infections (Anderson DW, Epstein JS, Lee TH, et al. Serologic confirmation of human T-lymphotropic virus type I infection in healthy blood and plasma donors. Blood 1989;74:2585–91; Lee TH, Coligan JE, McLane MF, et al. Serologic cross-reactivity between envelope gene products of type I and type II human T-cell leukemia virus. Proc Natl Acad Sci USA 1984;81:7579). While virus isolation and gene amplification techniques (Lee H, Swanson P, Shortly VS, Zack JA, Rosenblalt JD, Chen I. High rate of HTLV-II infection in seropositive IV drug abusers in New Orleans. Science 1989;244:471-5; De B, Srinivasan A. Detection of human immunodeficiency virus (HIV) and human lymphotropic virus type I or II dual infections by polymerase chain reaction. Oncogene 1989;4:1533–5) can differentiate HTLV-I from HTLV-II infection, these methods are labor intensive and require collection and processing of lymphocytes. A serologic assay that could distinguish the two infections is highly desirable. Such an assay would be very useful both for seroepidemiologic studies that have thus far been hampered by the inability to distinguish the two viruses and for the purpose of counseling blood donors and others who test seropositive (Chen ISY, Rosenblat JD, Black AC, Arrigo SJ, Green PL. 1990. HTLV-II Prevalence and regulation of gene expression. AIDS Res Hum Retroviruses 6:134–5).

Synthetic peptides representing .conserved "immunodominant" epitopes provide an attractive alternative to virus-derived antigens in view of their low cost and ability to be accurately reproduced. The analysis of antibodies reactive with predetermined amino acid sequences (Lerner RA. Antibodies of predetermined specificity in biology and medicine. Adv Immunol 1984;36:1–44) has been shown previously to be both a sensitive and specific means to distinguish related retrovirus infections from each other (Norrby E, Biberfeld G, Chiodi F, et al. Discrimination between antibodies to HIV and to related retroviruses using site directed serology. Nature 1987;329:248–50; Gnann JW, McCormick JB, Mitchell S, Nelson JA, Oldstone MBA. 1987. Synthetic peptide immunoassay distinguishes HIV type 1 and HIV type 2 infections. Science 237:1346–9). Because structural proteins such as env, gag and pol from both HTLV-I and HTLV-II are major immunodominant proteins under conditions of natural infection (Lee T, Coligan JE, Homma T, McLane MF, Tachibana N, Essex M. Human T-cell leukemia virus-associated membrane antigens (HTLV-MA): Identity of the major antigens recognized following virus infection. Proc Natl Acad Sci USA 1984;81:3856-60; Kanner SB, Mayer CC, Geffin RB, et al. Human retroviral env and gag polypetides; Serologic assays to measure infection. J Immunol 1986;137:674-8), the present inventors have analyzed the serologic reactivity of those regions of the env, gag and pol of HTLV-I and HTLV-II that exhibited considerable differences in the amino acid sequences (Sodroski J, Patarca R, Perkins D, et al. Sequence of the Envelope glycoprotein gene of Type II human T-lymphotropic virus. Science 1984;225:421-4).

U.S. Pat. No. 4,833,701 discloses a peptide composition having specific immunoreactivity to antibodies to HTLV-I.

SUMMARY OF THE INVENTION

One object of the present invention is to define a major immunodominant epitope of the HTLV proteins that does not show cross-reactivity with serum specimens from HTLV-II-infected individuals.

Thus, one embodiment of the present invention relates to a peptide having specific immunoreactivity to antibodies to HTLV-I, HTLV-II, or combinations thereof comprising a peptide selected from the group consisting of:

Env-1 (HTLV-I; a.a 191-214)LPHSNLDHILEPSIPWKSKLLTLV,
Env-2 (HTLV-II; a.a 187-210)VHDSDLEHVLTPSTSWTTKILKFI,
Env-5 (HTLV-I; a.a 242-257)SPNVSVPSSSSTPLLY,
Gag-1a (HTLV-I; a.a 102-117)PPSSPTHDPPDSDPQI,
Pol-3 (HTLV-I; a.a 487-502)-KQILSQRSFPLPPPHK, and
analogues thereof, wherein the amino acids in the sequence may be substituted as long as the immunoreactivity to antibodies to HTLV-I or HTLV-II derived from the three dimensional conformation of the sequences are substantially preserved.

The invention is further directed to an immunoassay method for the detection of antibodies to HTLV-I, HTLV-II or a combination thereof, a test kit for the detection of said antibodies, a peptide composition containing said peptides and a vaccine.

DETAILED DESCRIPTION OF THE INVENTION

Figure 1:
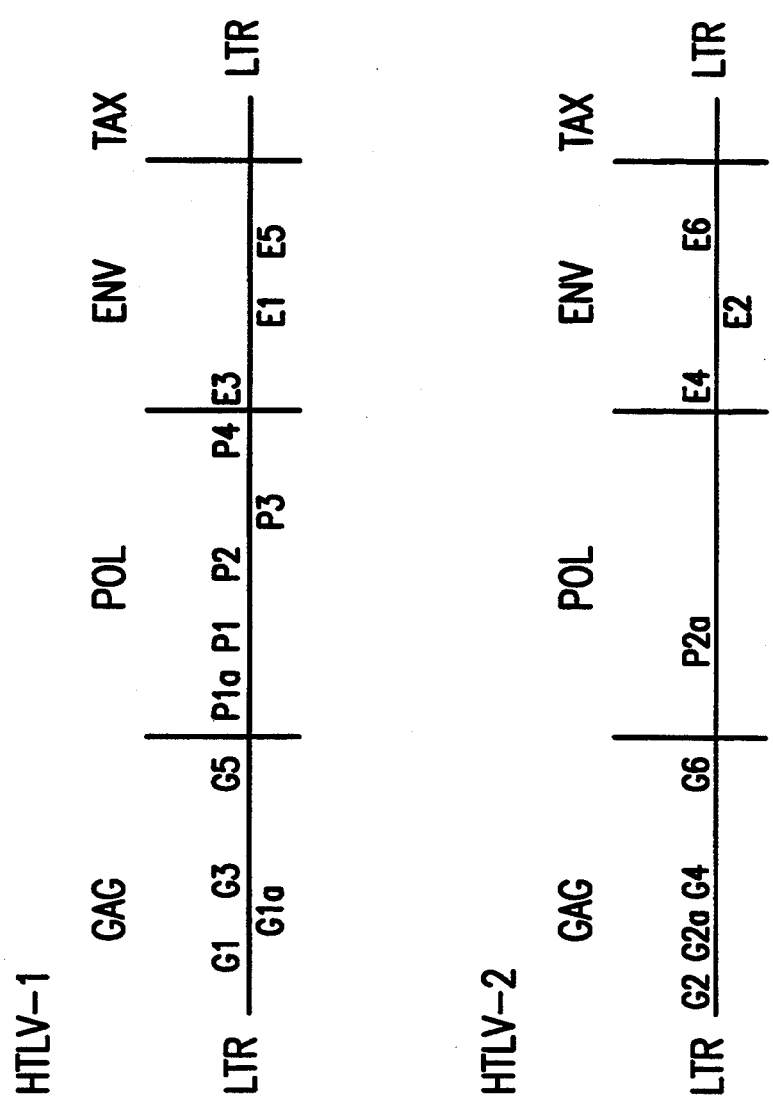
FIG. 1 shows the location of synthetic peptide in HTLV-1 genome upper panel and HTLV-II (lower panel). The relative position of each peptide is shown by the box.

The present invention relates to a highly sensitive method for the detection of antibodies to HTLV-I or HTLV-II in body fluids by the use of synthetic peptides. The peptides are also useful as a vaccine by stimulating the production of antibodies of HTLV-I or HTLV-II to provide protection against infection by HTLV-I or HTLV-II in healthy mammals, including humans. The peptides have amino acid sequences which correspond to segments on the envelope protein and are highly immunoreactive with antibodies in sera of patients infected with HTLV-I or HTLV-II. The detection method includes an enzyme-linked immunosorbent assay (ELISA), an immunoradiometric assay (IRMA), and other forms of immunoassay procedures such as enzyme immuno blotting assay on nitrocellulose paper and hemagglutination assay using the peptides as the antigen.

Immunoassays for HTLV need to be developed that satisfy two main criteria. A test must distinguish HTLV-I and HTLV-II in locales where both viruses are endemic. Enzyme immuno assays (EIA) where whole virus lysates are used as a source of antigens cannot effectively distinguish HTLV-I from HTLV-II due to the sequence homology in highly conserved regions of the core and the polymerase protein of these viruses. Two immunoassays must be available to laboratories involved in blood screening that are highly sensitive and specific. In the present study, the inventors report that synthetic peptides from immunoreactive domains of HTLV-I and HTLV-II viral proteins offer an approach to design an immunoassay that will distinguish HTLV-I from HTLV-II. The inventors also provide evidence that the synthetic peptide derived from the polymerase region of HTLV-I detects serum antibodies in most infected individuals.

Abbreviations for amino acids used herein are conventionally defined as described hereinbelow.

| Amino Acid | Three-letter abbreviation | One-letter symbol |
|---|---|---|
| Alanine | Ala | A |
| Arginine | Arg | R |
| Asparagine | Asn | N |
| Aspartic acid | Asp | D |
| Asparagine or aspartic acid | Asx | B |
| Cysteine | cys | C |
| Glutamine | Gln | Q |
| Glutamic acid | Glu | E |
| Glutamine or glutamic acid | Glx | Z |
| Glycine | Gly | G |

| Amino Acid | Three-letter abbreviation | One-letter symbol |
|---|---|---|
| Histidine | His | H |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

According to the present invention, peptides useful for the detection of antibodies to HTLV-I or HTLV-II are selected from the group consisting of:

Env-1 (HTLV-I; a.a 191-214)LPHSNLDHILEPSIPWKSKLLTLV,

Env-2 (HTLV-II, a.a 187-210)VHDSDLEHVLTPSTSWTTKILKFI,

Env-5 (HTLV-I; a.a 242-257)SPNVSVPSSSSTPLLY,

Gag-1a (HTLV-I; a.a 102-117)PPSSPTHDPPDSDPQI,

Pol-3(HTLV-I; a.a 487-502)-KQILSQRSFPLPPPHK, and analogues thereof, wherein the amino acids in the sequence may be substituted as long as the immunoreactivity to antibodies to HTLV-I or HTLV-II derived from the three dimensional conformation of the sequences are substantially preserved.

These peptides may comprise analogues or segments, i.e., a shorter or longer peptide chain by having more amino acids added to the terminal amino acids of the above sequence or having a few less of the terminal amino acids from either terminal. It is expected that as long as the three dimensional conformation recognizable by the dominant antibodies to HTLV-I or HTLV-II is preserved, analogues of the synthetic peptides may also comprise substitution and/or deletion of the recited amino acids of the above sequences.

Based on the high degree of sensitivity and specificity of the peptides according to the present invention in the immunoreaction of antibodies to HTLV-I or HTLV-II, it is believed that the peptides may also be useful as a vaccine (e.g., for ATL and HAM/TSP) and as immunogens for the development of both monoclonal and polyclonal antibodies to HTLV-I and HTLV-II in mammals, including humans. The peptides when coupled to a protein or a polymer carrier or when polymerized to homo or hetero dimers or high oligomers by cysteine oxidation, induced disulfide cross linking, or when polymerized to homo or hetero dimers or higher oligomers by use of homo or hetero functional multivalent cross linking reagents, can be introduced to normal subjects to stimulate production of antibodies to HTLV-I or HTLV-II and provide protection against infection in healthy mammals. Since the peptides according to the present invention are not derived biochemically from the virus, there is no danger of exposing the normal subjects who are to be vaccinated to the disease.

The advantages of using the peptides according to the present invention are many.

The peptides are chemically synthesized. This means that there is no involvement with the HTLV-I or HTLV-II virus at any time during the process of making the test reagent or the vaccine. During the preparation of the vaccine or the vaccination process, there is no risk of exposure of the production workers or individuals in the health profession to the HTLV-I or HTLV-II virus. Similarly, there is no risk or exposure to HTLV-I or HTLV-II in the use of these peptides or the development of monoclonal or polyclonal antibodies to HTLV-I or HTLV-II in mammals. Further, up to the final step of the test to detect antibodies to HTLV-I or HTLV-II, where the test reagent is exposed to samples of sera or body fluid, there is no risk of exposure of the laboratory worker to the HTLV-I or HTLV-II virus. Any risk of exposure in this final step can be further avoided by taking the precautionary step of heating the serum samples, which are to be tested, at 60° C. for half an hour, thereby deactivating the virus.

Another problem which is avoided by the process of the present invention is the possibility of false positive results caused by the presence of antigenic materials from host cells co-purified with the HTLV-I or HTLV-II viral preparation or E. coli derived proteins co-purified with expressed viral fragments. Certain normal individuals have antibodies to E. coli or human leukocyte antigens, e.g., HLA, which are cross reactive with the antigenic materials from host cells. Sera samples from these normal individuals even though they have not been exposed to HTLV-I or HTLV-II, may show a positive response in the ELISA or IRMA tests.

A diagnosis that a person may be infected with HTLV-I or HTLV-II based on this type of false positive response can bring severe anxiety to the person and his/her family. All of these problems can be avoided by using the peptides of the present invention as the test reagents.

Further, with appropriate amino acid analogue substitutions, it is expected that various peptide analogues based on the prescribed amino acid sequence can be synthesized with properties giving rise to lower background readings or better adsorption capacity to solid phases useful for HTLV-I or HTLV-II antibody screening assays.

Moreover, because the peptides of the present invention are synthetically prepared, the quality can be controlled and as a result, reproducibility of the test results can be assured. Also, since very small amounts of peptides are required for each test procedure, and because the expense of preparing the peptides is relatively low, the cost of screening body fluids for antibodies to HTLV-I or HTLV-II and the preparation of a vaccine is relatively low.

A method of detecting antibodies to HTLV-I, HTLV-II or combinations thereof in body fluids comprises preparing at least one of the above-mentioned peptides, analogues, or a mixture thereof, and using about 0.1 $\mu$g to about 20 $\mu$g, preferably about 1.0 $\mu$g to about 10 $\mu$g per test in a buffer at a pH of about 7.5 to 10, preferably about 9.4 to 9.8, of at least one peptide as the antigen in an immunoassay procedure.

The peptide prepared in accordance with the present invention can be used to detect HTLV-I and HTLV-II infection by using it as the test reagent in any form of immunoassay such as an enzyme-linked immunoadsorbent assay (ELISA), an enzyme immunodot assay, a hemagglutination assay, a immunoradiometric assay (IRMA), or any variety of competitive binding assays.

The present invention is further directed to an immunoassay method for the detection of antibodies to HTLV-I, HTLV-II or combinations thereof which comprises: (i) coating a solid support or other labeling material with an effective amount of a peptide of the invention for reacting with antibodies to HTLV-I, HTLV-II or combinations thereof in an amount sufficient to produce an antibody-peptide complex to be detected, (ii) adding a test sera diluted with a buffer wherein the antibodies to HTLV-I or HTLV-II in the test sera form a peptide-antibody complex with said peptide, (iii) incubating the mixture, and (iv) detecting the presence of the peptide-antibody complex. In step (iv), a second known antibody labelled with an enzyme and a substrate is introduced which reacts with the enzyme to form a colored product. Also, in step (iv), a second known antibody labelled with a radioactive element is introduced. Alternatively, in step (iv), the peptide antibody complex may also be detected by agglutination. The solid support may be further coated with at least one of the peptides in the invention in a multidot array. The amount of the peptide is preferably in the range of 1 μg to 10 μg per dot. The detection step (iv) may also be done competitively using labeled or unlabeled antigen or antibody to compete with the complex. The antigen of step (i) need not be attached in any way provided that the antibody-antigen complex may be detected such as by polyethylene glycol precipitation or by a Coombs reagent.

The invention is also directed to a test kit for the detection of antibodies to HTLV-I, HTLV-II, or combinations thereof, which comprises: a solid support or other suitable labeling material having attached thereto an immunoadsorbent comprising at least one peptide of the invention or simply said at least one peptide alone; a sample of normal serum as a negative control; a sample of serum containing antibodies of HTLV-I or HTLV-II as a positive control, and a buffer for diluting the serum samples.

Furthermore, the invention is directed to a peptide composition comprising at least one of the peptides of the invention. When more than one peptide is present in the composition, each is present in a ratio of 1:1 with respect to one another. For instance, when these peptides are present in the mixture, they are in a ratio of 1:1:1. Each peptide may be preferably present in an amount of 0.5 μg to 5 μg.

The invention is also directed to a vaccine containing at least one of the peptides of the invention and its uses to generate antibodies and other cells and products of the immune response.

Env-5 (HTLV-I; amino acids 242-257) is the most immunodominant epitope and reacts with all of the serum specimens from patients infected with HTLV-I with no cross-reaction from 35 persons infected with HTLV-II. Even though the number of samples tested in this study is small, they represent HTLV-I/II-infected patients from various clinical groups as well as various geographic disease-endemic areas, based on current estimated HTLV-I/II seroprevalence rate in blood donors (0.02%), the number for HTLV-I-positive subjects (n=52) would represent the number of similarly infected persons predicted for a population of 260,000.

The envelope protein of HTLV-I is known to show variability for different viral isolates (Daenke S, Nightingale S, Cruickshank JK, Bangham CRM. Sequence variants of human T-Cell lymphotropic virus type I from patients with Tropical Spastic Paraparesis and adult T-cell leukemia do not distinguish neurological from leukemia isolates. J Virol 1990;64:1278-82), and this could effect the sensitivity of the test. A comparison of the amino acid sequences of the Env-5 region (Ser-ProAsnValSerValProSerSerSerSerThr-ProLeuLeuTyr) with other viral isolates reveals that 13 of 16 (81%) amino acids are conserved. Preliminary data on epitope mapping of Env-5 suggest that the critical part of the epitope is not found at the three amino acid positions (amino acids 247, 250, and 251) that show variability.

The Env-1 peptide (HTLV-I; amino acids 191-215) demonstrates a high sensitivity for HTLV-I infection (92%), but a small percentage of HTLV-II infected subjects (8.6%) also reacts with this peptide, probably reflecting some degree of structural homology. Env-2 (HTLV-II; amino acids 187-210), on the other hand, reacts with both HTLV-I (94%) and HTLV-II (77%) serum samples. Thus, even though the peptide is chosen from a region within the HTLV-II sequence that has considerable differences in the amino acid sequence from the HTLV-I sequence, evidently, the epitope is mimicked in such a way that it is recognized by antibodies in both HTLV-I and HTLV--II infected serum specimens and could be included in future peptide assays for serologic determination of HTLV-I/II infection.

Other investigators have used recombinant proteins (Samuel KP, Lautenberger JA, Jorcyk CL, Joseph S, Wong-Staal F, Papas TS. Diagnostic potential for human malignancies of bacterially produced HTLV-I envelope protein. Science 1984;226:1094-7; Tachibana N, Miyoshi I, Papas TS, Essex M. Antibody reactivity to different regions of human T-cell leukemia virus Type I gp61 in infected people. J Virol 1989;63:4952-7) or synthetic peptide technology to identify antigenic sites on the envelope (Palker TJ, Tanner ME, Scearce RM, Streilein RD, Clark ME, Haynes BF. Mapping of immunogenic regions of human T-cell leukemia virus Type I (HTLV-I) gp46 and gp21 envelope glycoproteins with Env—encoded synthetic peptides and a monoclonal antibody to gp46. J Immunol 1989; 142:971-8; Copeland TD, Tsai WP, Kim YD, Oroszlan S. Envelope proteins of human T-cell leukemia virus type-I: characterization of antisera to synthetic peptides and identification of a natural epitope. J Immunol 1986;137:2945-51) proteins of HTLV-I. For example, one of our peptides (Env-1, amino acids 191-214) overlaps with a region of gp46 (amino acids 190-209) that contains both a T- and B-cell epitope (Palker TJ, Tanner ME, Scearce RM, Streilein RD, Clark ME, Haynes BF. Mapping of immunogenic regions of human T-cell leukemia virus Type I (HTLV-I) gp46 and gp21 envelope glycoproteins with Env—encoded synthetic peptides and a monoclonal antibody to gp46. J Immunol 1989;142:971-8; Copeland TD, Tsai WP, Kim YD, Oroszlan S. Envelope proteins of human T-cell leukemia virus type-I: characterization of antisera to synthetic peptides and identification of a natural epitope. J Immunol 1986;137:2945-51; Kurata A, Palker TJ, Streilein RD, Scearce RM, Haynes BF, Berzofsky JA. Immunodominant sites of human T-cell lymphotropic virus Type I envelope protein for murine helper T-cells. J Immunol 1989;143:2024-30). More recently, a recombinant fusion protein (MTA-4; 42 amino acids) reactive with a human monoclonal has been shown to specifically react only with HTLV-I infected serum samples (Foung SKH, Lipka JJ, Bui K. Determination of a unique and immunodominant epitope of HTLV-I. Presented at the 3rd Annual Conference of Retrovirology, Hawaii, 1990. (Abs)). The epitope of this monoclonal antibody has been mapped to amino acids 185-196 (Ralston S, Hoeprich P, Akita R. Identification and synthesis of the epitope for a human monoclonal antibody which can neutralize human T-cell leukemia/lymphotropic virus type I. J Biol Chem 1989;264:16343-6.), which overlaps with our Env-1 peptide. Plasmids containing sequences corresponding to the carboxyterminal region of HTLV-I gp46 plasmid pKS 300, amino acids 200-306 (Samuel KP, Lautenberger JA, Jorcyk CL, Joseph S, Wong-Staal F, Papas TS. Diagnostic potential for human malignancies of bacterially produced HTLV-I envelope protein. Science 1984;226:1094–7) and plasmid RP-C, amino acids 229–308 (Tachibana N, Miyoshi I, Papas TS, Essex M. Antibody reactivity to different regions of human T-cell leukemia virus Type I gp61 in infected people. J Virol 1989;63:4952–7) are recognized by antibodies from HTLV-I infected persons. Interestingly, the Env-5 synthetic peptide (amino acids 242–257) is contained within the regions encoded by the plasmids. These studies and the data presented here confirm that the C-terminal region of gp46 is highly immunogenic in humans. Of greater importance is the finding that serum specimens from HTLV-II-infected persons do not react with this epitope, thus defining an antigenic determinant at the C-terminal region of HTLV-I gp46 that is not shared by HTLV-II.

Thus, the Env-5 peptide-based assay provides a simplified, inexpensive, highly sensitive, and extremely specific test for discrimination of HTLV-I from HTLV-II infection, and could, therefore, easily replace the PCR procedure now used to distinguish the two viruses. The finding that the inventors can achieve enhanced diagnostic specificity by a peptide-based ELISA is supported by earlier reports demonstrating serologic discrimination of HIV-1 and HIV-2 infection (Norrby E, Biberfeld G, Chiodi F, et al. Discrimination between antibodies to HIV and to related retroviruses using site directed serology. Nature 1987;329:248–50; Gnann JW, McCormick JB, Mitchell S, Nelson JA, Oldstone MBA. 1987. Synthetic peptide immunoassay distinguishes HIV type 1 and HIV type 2 infections. Science 237:1346–9). Although the finding of specific immunodominant epitope(s) of HTLV-I has obvious diagnostic implications, it is also important to recognize the potential role this epitope may have in inducing T-cell proliferation or virus neutralizing antibodies.

The proteins encoded by the gag, pol, and env gene of HTLV contribute to many of the pathological and functional properties of the virus which may be relevant during the course of the infection and the progression of the disease (Hopp TP, Woods KR. Prediction of protein antigenic determinants from amino acid sequences. Proc Natl Acad Sci USA 1981;78:3824–8). Using a series of synthetic peptides with predicted antigenic epitopes from conserved amino-acid regions, the present inventors have tried to locate structural motifs within HTLV-I and HTLV-II for B-cell specific antibody recognition. Of the various peptides derived from the gag and pol region of both HTLV-I and HTLV-II, only two react with serum specimens from HTLV-I/II infected individuals. Gag-1a defined from the C-terminal of p19 protein (HTLV-I; aa 102–117) is the most immunodominant epitope and reacts with 90% of the HTLV-I infected sera subjects; a small percentage of HTLV-II infected sera also react with this peptide (11%), reflecting some degree of antigenic homology within the HTLV-I and HTLV-II.

Furthermore, serum antibody reactivity against Gag-1a can be specifically inhibited with HTLV-I which represents a conformationally "native" epitope present on the HTLV-I. Therefore, the Gag-1a peptide with amino acid sequence Pro Pro Ser Ser Pro Thr His Asp Pro Pro Asp Ser Asp Pro Gln Ile represents an immunodominant domain of HTLV-I that is recognized by serum antibodies from most of HTLV-I infected persons. Moreover, the Gag-1a based immunoassay allows a serologic distinction between the closely related HTLV-I and HTLV-II infections.

The immunodominance of the C-terminal region of p19 gag protein ties together with two other findings. Palker et al (Palker, T, J., Scearce, R, M., Copeland, T, D., Oroszlan, S., and Haynes, B, F., 1986. C-terminal region of human T-cell lymphotropic virus type I (HTLV-I) p19 core protein is immunogenic in humans and contains an HTLV-I specific epitope. J. Immunol., 136, 2393–2397) have described an epitope at the C-terminus of p19 down stream from our Gag-1a which reacts with 6 of the 8 serum specimens tested. In their study, only 2 of 8 specimens show reactivity to the epitope which overlaps with Gag-1a and can be due to the sensitivity of the test system used in their study. More recently, Kuroda et al (Kuroda, N., Washitani, Y., Shiraki, H., Kiyokawa, H., Ohno, M., Sato, H., and Maeda, Y., 1990. Detection of antibodies to human T-lyphotropic virus type I by using synthetic peptides. Int. J. Cancer, 45, 865–868) have reported an immunodominant epitope contained within the amino acids 100–130 at the C-terminus of p19 which reacts with 100% of their HTLV-I infected serum specimens. The specificity of this peptide for HTLV-II infected serum specimens is not tested in their study. These studies and the data presented here confirm that the C-terminal region of p19 is highly immunogenic and further demonstrate that the C-terminus of p19 contains a strain specific epitope which is HTLV-I specific.

In natural infection with a retrovirus, the host generally makes antibodies to the products of the gag or env gene or both (Schupbach, J., Kalynaraman, J., Sarngatiaran, G., Blattner, W., and Gallo, R., 1983. Antibodies against three purified proteins of human types C retroviruses, human T-cell leukemia-lymphoma virus, in adult T-cell leukemia-lymphoma patients and healthy blacks from the Caribbean, Cancer Res 43, 886–891.; Gallo, D., Hoffman, M, N., Lossen, C, K., Diggs, J, L., Hurst, J, W., and Penning, L, M., 1988. Comparison of immunofluorescence, Enzyme immunoassay and western blot (immunoblot) methods for detection of antibody to Human T-cell leukemia virus Type-I, J. Clin Microbiol, 26, 1487–1491). Antibody responses to the products of the pol gene during HTLV-I/II infection have not been described. The results presented here demonstrate that the majority of individuals infected with the HTLV-I and HTLV-II have readily detectable levels of antibodies to the peptide derived from the central region of the pol gene. The results presented here clearly indicate that similar to antibody responsiveness to pol gene products during HIV infection, HTLV-I pol products also induce antibody responses. The antisera raised to this peptide would help to evaluate the structural characteristics of pol products.

EXAMPLE 1

METHODS

A total of 186 serum specimens from various study groups are chosen for this study (Table 1).

TABLE 1

Standard serologic results and PCR data of study population

| Group | No. tested | Serology HTLV-I/II | HIV-1 | PCR Confirmation Group HTLV-I | HTLV-II |
|---|---|---|---|---|---|
| HTLV-I | | | | | |
| U.S. residents* | 20 | + | − | + | − |
| Japanese | 32 | + | − | ND** | ND |
| HTLV-II | 35 | + | − | − | + |
| U.S. residents | | | | | |
| HIV-1 | 28 | − | + | ND | ND |
| U.S. residents | | | | | |
| Other*** | 50 | − | ND | ND | ND |
| Normal | 21 | − | − | ND | ND |

*Two of the persons within the groups were of Caribbean origin.
**ND - not determined
***Serum from patients with non retroviral infection.

The sera includes 87 specimens from subjects who are seropositive to HTLV-I/II. With the exception of 32 specimens kindly provided by Dr. M. Osame, Kagoshima, Japan, all of the serum specimens are determined to be from HTLV-I or HTLV-II-positive persons by polymerase chain reaction (PCR) assays (De B, Srinivasan A. Detection of human immunodeficiency virus (HIV) and human lymphotropic virus type I or II dual infections by polymerase chain reaction. Oncogene 1989;4:1533-5), using peripheral blood lymphocytes from these same persons. Of these 55 PCR-confirmed specimens, 20 are from persons infected with HTLV-I whereas the other 35 are from persons infected with HTLV-II. Of the 20 HTLV-I-infected subjects, 13 have either ATL or HAM/TSP syndrome, and the other 7 are asymptomatic blood donors. The HTLV-II-infected subjects are mostly intravenous drug users. Twenty serum specimens within this group are obtained from commercial sources (Serologics, Inc., Marietta, Ga.).

For comparison, serum specimens from 28 patients with confirmed human immunodeficiency virus (HIV) infection manifesting as asymptomatic (n=10) or acquired immunodeficiency syndrome (AIDS) (n=18) are tested. Serum specimens from patients with a variety of other clinical diseases (n=50) are used to test for non-specific interference (Anderson DW, Epstein JS, Lee TH, et al. Serologic confirmation of human T-lymphotropic virus type I infection in healthy blood and plasma donors. Blood 1989;74:2585-91). These specimens include those with rheumatoid factor (n=3), nuclear antibodies (n =3) and anti—HLA—DR antibodies (n=1), those with viral infection (cytomegalovirus, n=3; Epstein-Barr virus, n=3; herpes simplex virus, n=3; hepatitis B virus, n=4; and rubella virus, n =3) and those with parasitic infection (*Plasmodium falciparum*, n=3; *Toxoplasma gondii*, n=3; *Trypanosoma cruzi*, n=5; *Schistosoma mansoni*, n=5; *Strongyloides stercoralis*, n=6; and *Wuchereria bancrofti*, n=5). Serum specimens from 21 normal blood donors serve as a negative control.

REFERENCE HTLV AND HIV ANTIBODY TESTS

Patients serum specimens are initially tested for HTLV-I antibodies with a commercial enzyme-linked immunosorbent assay (HTLV-I ELISA, Dupont, Wilmington, Del.), according to the manufacturer's recommendations. Specimens that are repeatedly reactive are further tested by Western blotting and radioimmunoprecipitation assay as described previously (Hartley TM, Khabbaz RF, Cannon RO, Kaplan JE, Lairmore MD. Characterization of antibody reactivity to human T-cell lymphotropic virus types I/II using immunoblot and radioimmunoprecipitation assays. J Clin Microbiol 1990;28:646-50). Briefly, purified HTLV-I antigen (MT-2 cell line, Miyoshi I, Kubonishi I, Yoshimoto S, et al. Type C virus particles in a cord T-cell line derived by co-cultivating normal human cord leukocytes and human leukemia T-cells. Nature 1981;296:770-3) obtained from Hillcrest Biologicals, Cypress, Calif., is diluted in sodium dodecyl sulfate sample buffer (0.125 M Tris HCl, pH 6.8, 5% 2ME, 4% SDS), boiled for 3 min and electrophoresed in a 10% polyacrylamide gel with a 3% stacking gel. The separated proteins are electroblotted onto nitrocellulose paper. Individual strips are incubated with 1:100 dilution of serum, washed, and incubated for 1 h with 5 ug of biotinylated goat anti-human (heavy- and light-chain) immunoglobulin G (Vector Laboratories, Burlingame, Calif.) per ml. Following reaction with an avidin-biotin-horseradish peroxidase conjugate and further washing, immune reactions are visualized with diaminobenzidine-nickel chloride-hydrogen peroxide as a substrate. For radioimmunoprecipitation assay, MT-2 cell lines are metabolically labeled (200 uCi of each amino acid/$10^7$ cells/ml) with [$^{35}$S] cysteine and [$^{35}$S] methionine (New England Nuclear, Boston, Mass.). The labeled cells are washed in phosphate-buffered saline (PBS) and extracted in PBS containing 0.1% SDS and 0.02% Triton X-100. The detergent solubilized proteins are reacted with serum specimens, immune complexes precipitated by Protein-A Sepharose (Sigma, St. Louis, Mo.), run on a 10% polyacrylamide gel followed by autoradiography of the dried gel (Hartley TM, Khabbaz RF, Cannon RO, Kaplan JE, Lairmore MD. Characterization of antibody reactivity to human T-cell lymphotropic virus types I/II using immunoblot and radioimmunoprecipitation assays. J Clin Microbiol 1990;28:646-50). A serum specimen is determined to be HTLV-I/II-positive if antibody reactivity is detected to at least two different HTLV structural gene products (gag p24 and env gp46 and/or gp68) either by Western blotting or RIPA analysis. Serum specimens reacting with only gag or env gene products are considered indeterminate and are not included in this study.

The antibodies to HIV proteins are determined by both ELISA and Western blot (Dupont), and only those specimens having antibodies to both gag and env proteins are included.

POLYMERASE-CHAIN REACTION ASSAYS

PCR is performed with total genomic DNA isolated from patients' peripheral blood lymphocytes by using reaction conditions as described previously (Saiki R, Gelfand, Stoffel S, et al. Primer directed enzymatic amplification of DNA with a thermostable DNA polymerase. Science 1988;239:487-9). Oligonucleotide primer pairs from pol and gag genes of HTLV-I and HTLV-II are used to amplify 1 ug total genomic DNA for each PCR amplification (De B, Srinivasan A. Detection of human immunodeficiency virus (HIV) and human lymphotropic virus type I or II dual infections by polymerase chain reaction. Oncogene 1989;4:1533-5.; De B, Srinivasan A. Multiple primer pairs for the detection of HTLV-I by PCR. Nucleic Acids Res 1989;17:2142). The amplified products are analyzed on a 5.0% polyacrylamide gel and confirmed further by Southern blot hybridization, using specific pol and gag nucleotide $^{32}$p labeled probes. Genomic DNA preparation from MT-2 cells (HTLV-I), MO-T (HTLV-II), and Hut-78 (uninfected) are used as controls. A sample is defined as HTLV-I-or HTLV-II-positive based on its reactivity with primer pairs in two separate gene products.

PEPTIDE SELECTION AND SYNTHESIS

Using published amino acid sequences (Myers G, Josephs SF, Rabson AB, Smith TF, Wong Staal F. In: Human retroviruses and AIDS. Los Alamos National Laboratory, Los Alamos, N.M. 1988), the inventors aligned HTLV-I and HTLV-II sequences in their envelope regions. Four peptides are selected for synthesis by identifying regions in which HTLV-I and HTLV-II shows considerable amino acid differences (FIG. 1). A cysteine residue is added to the N-terminus of each peptide to facilitate conjugation with proteins for studies not reported here. Secondary structure characteristics of the envelope protein are predicted (Chou PY, Fasman GD. Prediction of the secondary structure of proteins from their amino acid sequence. Adv Enzymol 1978;47:45) by entering amino acid sequences into the "Pepplot" program (M. Gribskov, University of Wisconsin, Madison Wisc.), and hydrophilicity characteristics are calculated by the method of Hopp and Woods (Hopp TP, Woods KR. Prediction of protein antigenic determinants from amino acid sequences. Proc Natl Acad Sci USA 1981;78:3824–8).

Synthetic peptides are made on the MilliGen 9050 Pepsynthesizer with 9-fluorenylmethyloxycarbonyl (Fmoc) chemistry, using the manufacturer's reagents and recommended chemistry cycles. Peptides are cleaved from the resin, precipitated, and extracted several times with anhydrous ether. Final purification is by preparative high performance liquid chromatography (HPLC) on a Waters C18 Delta-Pak (19 mm×30 cm, 15u particle, 300u pore size), using 0.1% trifluoroacetic acid (TFA) in water as the starting solvent followed by a 0–50% acetonitrile gradient in 0.1% TFA. Amino acid composition, amino acid sequence analysis, and analytical reverse phase HPLC are performed to confirm peptide sequence and purity.

QUANTITATIVE ASSESSMENT OF ANTIBODIES TO SYNTHETIC PEPTIDES

Polyvinyl plates (Immulon II, Dynatech Laboratories, Inc., Alexandria, Va.) are coated with 50 ul of synthetic peptides (100 ug/ml) in 0.01M carbonate buffer, pH 9.6, and incubated overnight at 4° C. The plates are washed with PBS containing 0.05% Tween-20 (PBS-T) six times, and each well is incubated with 200 ul of 3% bovine serum albumin (BSA) in PBS-T for 1 h at 37° C. to block excess reactive sites. After the wells are washed, a 1:20 dilution of each test serum is added to duplicate wells and the plates are incubated for 90 min at 37° C. and rinsed with PBS-T. Alkaline phosphatase conjugated, goat anti human IgG (Sigma, St. Louis, Mo.) is added and incubated for 90 min at room temperature, followed by addition of p-nitrophenyl phosphate (Sigma) substrate. The plates are read with an ELISA reader (SLT Lab Instrument, Austria) at 405, nm. Each serum specimen is also assayed in plates coated with BSA or unrelated synthetic peptide to control for nonspecific antibody binding. Seropositivity is defined as any value greater than the mean of the normal controls +3 standard deviations.

COMPETITIVE INHIBITION ASSAY

Inhibition of antibody binding to the synthetic peptide is carried out by adding increasing concentrations of synthetic peptide or purified HTLV-I or HTLV-II antigen (1-10 ug/ml) in the ELISA. The serum is mixed with the inhibition antigen immediately before it is added to the Env-5 peptide-coated plate, followed by assay as described above. The results are expressed as the percentage inhibition of antibody binding.

STATISTICAL ANALYSIS

Student's t-test is used for statistical evaluation as noted.

RESULTS

Quantitation of Human Antibodies to Synthetic Peptide

A non-competitive enzyme linked immunosorbent assay (ELISA) is developed using synthetic peptides (Env-1, Env-2 and Env-5) as a solid phase to detect strain-specific antibodies in HTLV-I/II infected subjects. In a series of experiments (data not shown), the interassay and intra-assay coefficient of variation (CV) are less than 15% and less than 8%, respectively. When this assay configuration is used to detect antibodies in a panel of serum specimens from patients infected with HTLV-I or HTLV-II, the highest percentage (100%) of seropositivity in the HTLV-I group is seen for Env-5, Env-1, Env2, Gag-1a and Pol-3.

TABLE 2

Reactivity of serum specimens to synthetic peptides.

| Group | No. tested | No. Positive* | | | | |
|---|---|---|---|---|---|---|
| | | Env-1 | Env-2 | Env-5 | Gag-1a | Pol-3 |
| HTLV-I | 52 | 48(92)** | 49(94) | 52(100) | 50(96) | 50(96) |
| HTLV-II | 35 | 3(8.5) | 27(77) | 0(0) | 6(11.5) | 34(88) |
| HIV-1 | 28 | 0(0) | ND*** | 0(0) | 0(0) | 0(0) |
| Other Infection | 34 | 0(0) | ND | 0(0) | 0(0) | 0(0) |
| Controls | 21 | 0(0) | 0(0) | 0(0) | 0(0) | 3(14) |

*Positive value defined by O.D higher than the mean +3 S.D of 21 normal controls.
**Number in parenthesis is percent positive.
***ND - not determined.

None of the 35 HTLV-II-infected serum specimens react with Env-5.

Env-1 demonstrates a high degree of reactivity (48/52; 92%) with serum specimens from HTLV-I infected persons and some cross-reaction (3/35; 8.6%) with specimens from HTLV-II-infected persons. Env-2, although derived from HTLV-II sequence, reacts strongly with serum specimens from both HTLV-I (49/52; 94%) and HTLV-II (27/35; 77%) infected persons. Of the 21 serum specimens from normal controls and the 78 specimens from subjects with other infections, including HIV, none react with any of these peptides.

One of the synthetic peptides termed Gag-1a (HTLV-I; a.a 102–117) derived from the Gag encoded protein of HTLV-I, demonstrates a high degree of reactivity (47/52;90%) with serum specimens from HTLV-I infected persons and some cross reaction (4/35;11%) with specimens from HTLV-II infected persons (Table-2). Of the six peptides derived from the pol encoded gene proteins, only pol-3 (HTLV-I; a.a 487–502) reacts with both HTLV-I (50/52; 96%) and HTLV-II (30/35; 86%) infected serum specimens.

Specificity of antibodies detected by Env-5

Figure 2A:
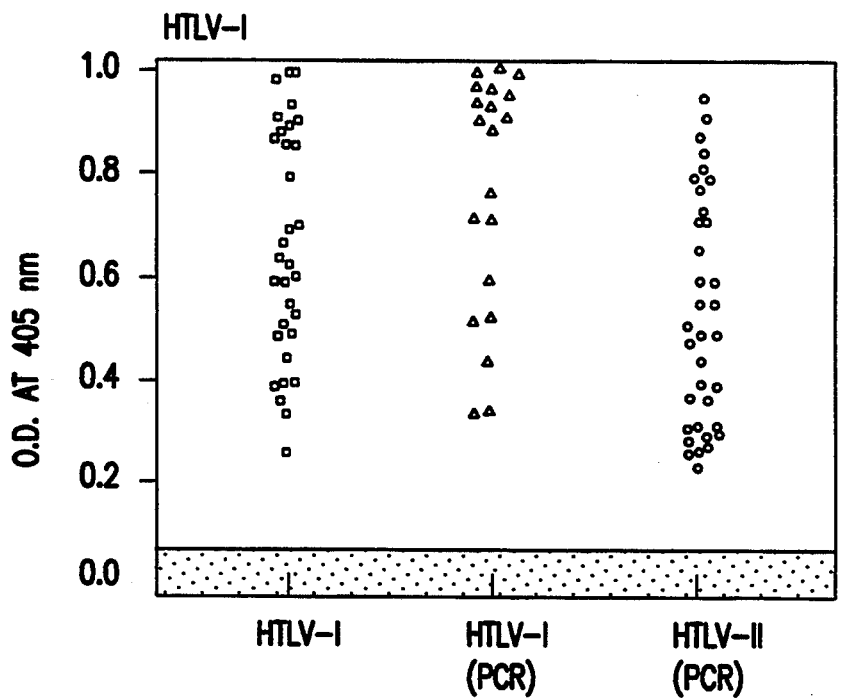
FIG. 2 shows antibodies to purified HTLV-I protein (upper panel) or Env-5 peptide (lower panel) in patients with HTLV-I infection (HTLV-I), with HTLV-I infections that have been confirmed by PCR (HTLV-I PCR) and with HTLV-II infection that have been PCR confirmed (HTLV-II PCR). The shaded area represents the mean + 3 SD of the responses of 21 normal persons.
Figure 2B:
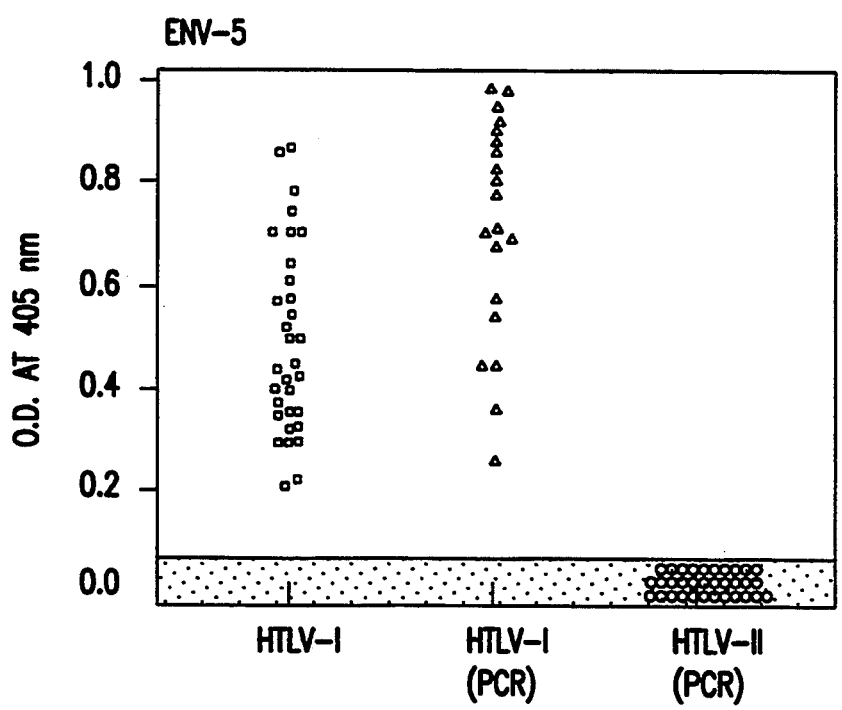

Serologic cross-reactivity of serum specimens from HTLV-I and HTLV-II-infected patients is well documented (Anderson DW, Epstein JS, Lee TH, et al. Serologic confirmation of human T-lymphotropic virus type I infection in healthy blood and plasma donors. Blood 1989;74:2585–91.; Lee TH, Coligan JE, McLane MF, et al. Serologic cross-reactivity between envelope gene products of type I and type II human T-cell leukemia virus. Proc Natl Acad Sci USA 1984;81:7579). Since the present inventors observe a high degree of sensitivity (100% for HTLV-I) and specificity (no cross-reaction with HTLV-II) with the Env-5 based assay, they wanted to confirm that the HTLV-II-infected study population indeed contains antibodies that cross-react in standard serologic assays which utilize HTLV-I viral antigen. All 35 serum specimens from HTLV-II-infected subjects have levels of antibody to HTLV-I ($>3$ SD above the mean for 21 normal controls) and there is no significant difference in the antibody levels between these HTLV-I-infected subjects and persons infected with HTLV-II ($P>0.05$) (FIG. 2). When these specimens from HTLV-II-infected subjects are tested in the Env-5 based immunoassay, the cross-reactivity seen in the serologic assay for HTLV-I is no longer observed (FIG. 2). This markedly enhanced specificity of the Env-5 assay has absolutely no effect on the diagnostic sensitivity of the test. Among the 32 serum specimens from HTLV-I-infected asymptomatic Japanese patients and 20 serum specimens from HTLV-I infected persons (confirmed by PCR), all are positive in the Env-5 assay. Further, there is no statistically significant difference ($P>0.05$) in the antibody levels to Env-5 between Japanese asymptomatic patients and HTLV-I-infected, PCR-confirmed patients.

Figure 3:
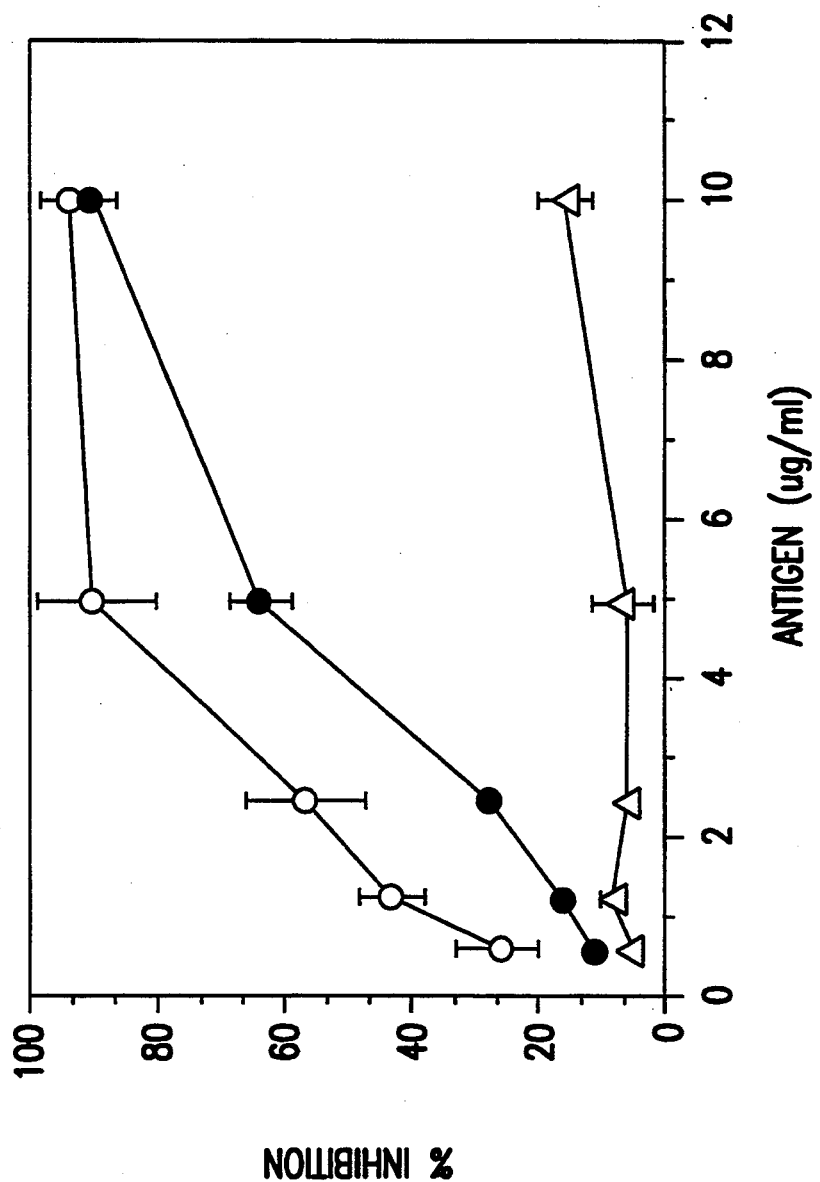
FIG. 3 shows the competitive inhibition by Env-5 (●—●), HTLV-I (O—O) or HTLV-II (Δ—Δ) purified proteins of anti-Env-5 antibodies in HTLV-I infected individuals. Serial 1:2 dilutions of a 10 ug/ml peptide or HTLV proteins solution are mixed 1:1 with a 1:10 dilution of test serum. The mixtures are allowed to incubate overnight at 4° C. Each is then assayed for anti-Env-5 activity by ELISA. The results are expressed as the mean percentage inhibition of four HTLV-I infected sera.

To further demonstrate the specificity of Env-5, the present inventors next performed a competitive inhibition experiment with serum specimens from four HTLV-I infected patients by preincubating the serum specimens with Env-5 peptide, and HTLV-I and HTLV-II antigen. The antibody reactivity against Env-5 could be specifically inhibited by preincubating the serum specimen with Env-5 peptide or HTLV-I protein in a dose dependent manner, whereas incubation with a HTLV-II protein or unrelated peptide does not show any inhibition (FIG. 3).

Distribution of Antibodies to Gag-1a and Pol-3

Figure 4B:
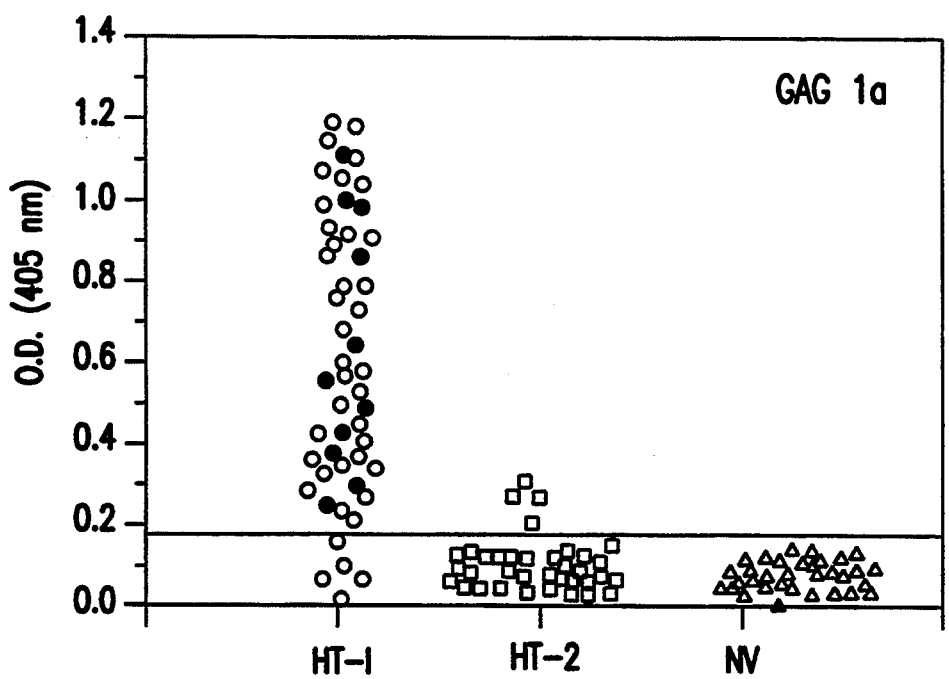
FIG. 4 shows IgG antibodies to Gag-1a (upper panel) or Pol-3 (lower panel) peptide in patients with HTLV-I infection (o), HTLV-II (□) infection and normal controls (Δ). The shaded symbol in the HTLV-I infected group represents antibody responsiveness of the individuals with HAM/TSP or ATL.
Figure 4A:
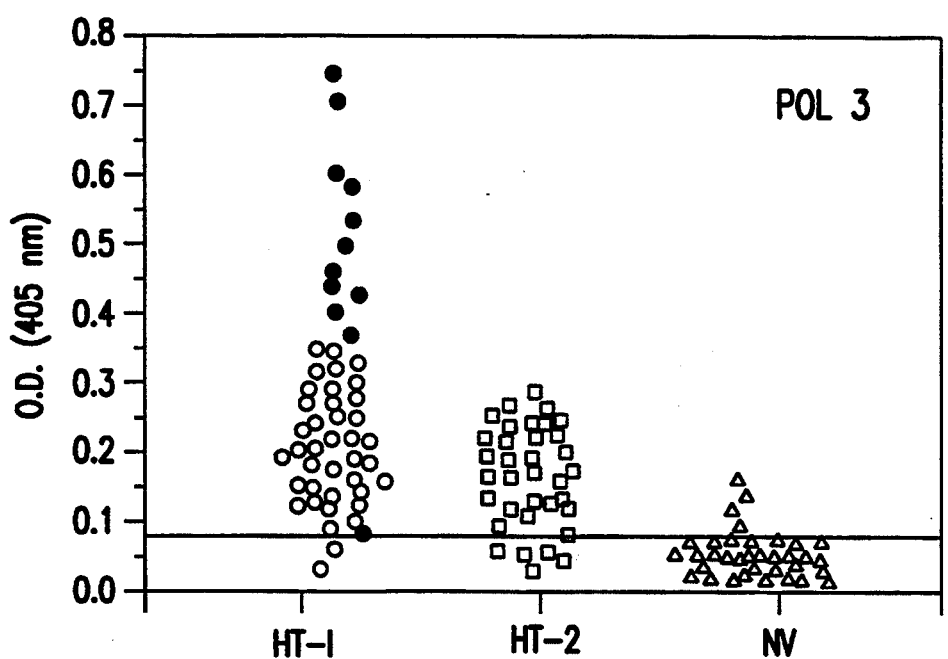

To evaluate the relative distribution of antibodies, serum levels of antibodies to peptides are compared in HTLV-I infected (asymptomatic and those with HAM/TSP), HTLV-II infected (asymptomatic) and normal controls. Most of the reactivity for Gag-1a antibodies is found in the HTLV-I infected group (FIG. 4). Within this group, there is no significant difference in the levels of antibodies to Gag-1a in those who are asymptomatic and those with HAM/TSP ($p>0.05$). In contrast, seroreactivity of Pol-3 was significantly higher in patients with HAM/TSP when compared with HTLV-I asymptomatic individuals (FIG 4). A significant proportion of serum specimens from HTLV-II reacts with this peptide and the levels of antibodies are similar to levels in HTLV-I infected asymptomatic individuals. In addition, four of the 35 serum specimens from normal donors demonstrate low levels of reactivity to Pol-3.

Antigenic Index Characteristics of Gag-1a and Pol-3

Figure 5:
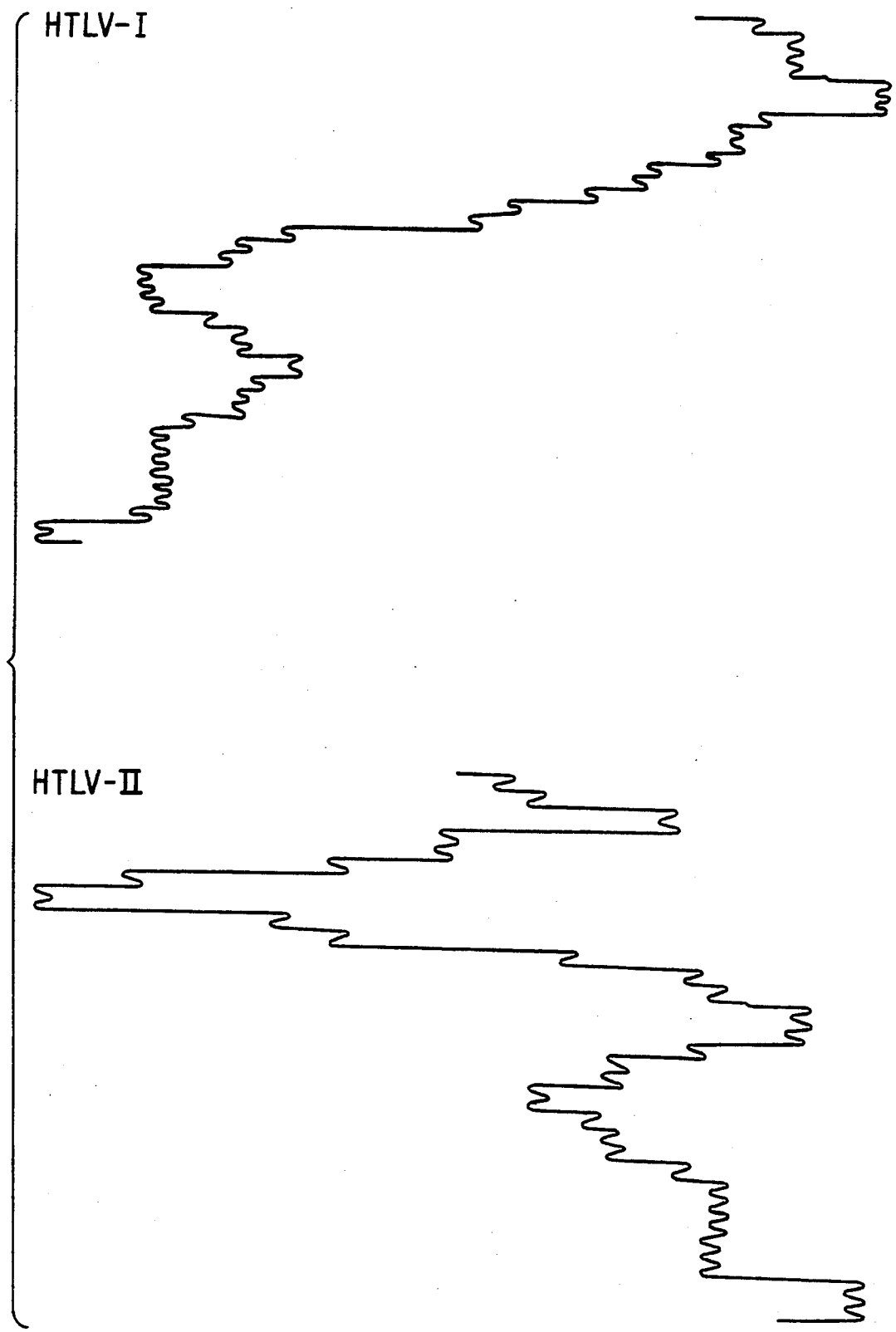
FIG. 5 shows a computer prediction of the secondary structure of gag encoded protein of HTLV-I (Top) and HTLV-II (bottom) superimposed with the value for antigenic index. The radius of a circle over a residue is proportional to the mean antigenic index as calculated for the residue plus the next five residues. The parameters for hydrophilicity, flexibility and surface probability are averaged over five amino acid residues, with a limit of 0.7 for hydrophilicity, 1.04 for flexibility and 5.0 for surface probability.

The secondary structure characteristics of gag and pol protein of both HTLV-I and HTLV-II are analyzed by using computer algorithms developed by Chou and Fasman (Chou, P, Y., Fasman, G, D., 1978. Prediction of the secondary structure of proteins from their amino acid sequence. Adv Enzymol, 47, 47). FIG. 5 shows a secondary structure prediction for the gag region of HTLV-I and HTLV-II. Superimposed on the structural backbone are domains of high antigenic indices. The antigenic index is an algorithm designed by Jameson and Wolf to predict surface domains for combined values of flexibility, hydrophilicity and (Chou, P, Y., and Fasman, G, D., 1974. Prediction of Protein Confirmation. Biochemistry, 13, 222–244). One of the four regions with high antigenic indices lies within the Gag-1a domain. The other three antigenic determinants are located near the c-terminus (amino acid numbers 337–342; 390–395 and 402–408). The three highest antigen index domains within HTLV-II gag are located at the amino acid positions 343–348; 403–408 and 405–411. The absence of such a structural motif within the HTLV-II sequence (FIG. 5) most likely is responsible for the lack of antibody responsiveness to this peptide in sera from individuals infected with HTLV-II. A similar analysis of pol protein of HTLV-I demonstrates Pol-3 to be located in an area of high hydrophilicity and antigenic index. In contrast, although other peptides such as Pol 1a and Pol-4 demonstrate high antigenic index, less than 10% of sera from infected individuals react with these peptides (data not shown).

In the following examples, 0.25% by weight of glutaraldehyde may be added in the coating buffer to facilitate better peptide binding on the plates or beads. Further, horseradish peroxidase conjugated mouse monoclonal anti-human IgG antibody may be used in place of horseradish peroxidase conjugated goat anti human IgG (Fc) as the second antibody tracer.

The gelatin used in these processes can include calf skin gelatin, pig skin gelatin, fish gelatin or any known available gelatin proteins or be replaced with albumin proteins.

EXAMPLE 2

Detection of Antibodies to HTLV-I or HTLV-II by an Enzyme-Linked Immunoadsorbent Assay.

Wells of 96-well plates are coated at 4° C. overnight (or 3 hours at room temperature), with at least one of the peptides of the invention at 1.5 ug per well of the mixture in 100 ul 10 mM NaHCO3 buffer, pH 9.5. The wells are washed three times with phosphate buffered saline (PBS) and then incubated with 250 ul of 3% by weight of gelatin in PBS at 37° C. for 1 hour to block nonspecific protein binding sites, followed by three more washes with PBS containing 0.05% by volume of Tween 20. The test sera (blood taken from a human patient or normal individual) are diluted with PBS containing 20% by volume normal goat serum, 1% by weight gelatin and 0.05% by volume Tween 20 at dilutions of 1:20 and 1:200, volume to volume, respectively. 200 ul of the diluted sera are added to each well and allowed to react for 1 hour at 37° C. The wells are washed three times with 0.05% by volume Tween 20 in PBS in order to remove unbound antibodies. Horseradish peroxidase conjugated goat anti-human IgG (Fc) is used as a second antibody tracer to bind with the HTLV-I or HTLV-II antibody-antigen complex formed in positive wells. 100 ul of peroxidase labeled goat antihuman IgG at a dilution of 1:3000 in 1% by volume normal goat serum, 0.05% by volume Tween 20 in PBS is added to each well and incubated at 37° C. for another 15 minutes.

The wells are washed five times with 0.05% by volume Tween 20 in PBS to remove unbound antibody and reacted with 100 ul of the substrate mixture containing 0.04% by weight orthophenylenediamine (OPD) and 0.012% by volume hydrogen peroxide in sodium citrate buffer, pH 5.0. This substrate mixture is used to detect the peroxidase label by forming a colored product. Reactions are stopped by the addition of 100 ul of 1.0M $H_2SO_4$ and the absorbance measured using an ELISA reader at 492 nm (i.e., $A_{492}$). Assays are performed in duplicate with one dilution (1:20) of serum samples from normal individuals or from patients with diseases unrelated to HTLV-I or HTLV-II infection used as negative controls. Absorbance readings greater than the cutoff value of $A_{492}=0.12$, (about 3×the mean $A_{492}$ value of normal serum control are taken as positive).

EXAMPLE 3

The procedure of Example 2 is repeated using the same sera samples as in Example 2 except that the well plates are precoated with 1 ug per well heat inactivated NP40 solubilized HTLV-I.

EXAMPLE 4

Detection of Antibodies of HTLV-I or HTLV-II by an Immunoradiometric Assay (IRMA)

Wells of 96-well flexible-polyvinylchloride (PVC) plates are coated at 4° C. overnight (or 3 hours at room temperature) with at least one of the peptides of the invention at 1.5 ug per well in 100 ul 10mM NaHCO3 buffer, pH 9.5. The wells are washed three times with phosphate buffered saline (PBS) and then incubated with 250 ul of 3% by weight gelatin in PBS at 37° C. for 1 hour to block the non-specific protein binding sites, followed by three or more washes with PBS containing 0.05% by volume Tween 20. The test sera (blood taken from a human patient or normal individual) are diluted with PBS containing 20% by volume normal goat serum, 1% by weight gelatin and 0.05% by volume Tween 20 at dilutions of 1:20 and 1:2000 (volume to volume) respectively. 200 ul of the diluted sera are added to each well and allowed to react for 1 hour at 37° C. The wells are then washed three times with 0.05% by volume Tween 20 in PBS in order to remove unbound antibodies. I-125 labeled affinity purified goat antihuman IgG(Fc) is used as a second antibody tracer that binds with the antibody-antigen complex formed in positive wells. 100 ul of I-125 labeled goat antihuman IgG of 50,000–200,000 cpm in 1% by volume normal goat serum, 0.05% by volume Tween 20 in PBS is added to each well and incubated at 37° C. for another hour.

The wells are washed five times with 0.05% to volume Tween-20 in PBS to remove unbound second antibody and dried. The wells are cut and counted by a gamma-scintillation counter. Assays are performed in duplicate with a 1:20 dilution volume to volume. Normal sera sample as negative controls are also tested simultaneously. Cpm readings greater than the average reading of normal sera samples +4SD (standard deviation) are taken as positive.

EXAMPLE 5

Detection of Antibodies to HTLV-I or HTLV-II by a Hemagglutination Assay using at least one of the peptides of the invention coated gelatin articles, Erythrocytes of different animal species or latex beads as the solid phase immunoadsorbent.

One ml thoroughly washed erythrocytes, gelatin particles, or polystyrene latex beads are coated with at least one of the peptides of the invention at concentrations in the range of 5 ug/ml to 1 mg/ml. The peptide mixture coated cells, particles or beads are then incubated with serially diluted serum samples in the wells of a 96-well U-shaped microplate. After being left at room temperature for about an hour, the agglutination patterns on the bottom are read and the largest dilution showing a positive reaction is recorded.

This is a one-step assay which could be used for both qualitative and quantitative analysis of the presence of antibodies to HTLV-I or HTLV-II in specimens including sera or biofluids.

EXAMPLE 6

A third test kit for detecting HTLV-I or HTLV-II antibodies using the hemagglutination assay comprises a compartmented enclosure containing multiple 96-well U-shaped microplates and materials for hemagglutination assay including (1) a bottle containing erythrocytes, gelatin particles or latex polystyrene beads coated with at least one of the peptides of the invention; (2) normal human serum (as a negative control); and (3) heat inactivated, seropositive HTLV-I or HTLV-II serum (as a positive control). The procedure described in Example 5 is to be followed.

EXAMPLE 7

A diagnostic test kit for HTLV-I or HTLV-II antibody detection can be constructed. The test kit comprises a compartmented enclosure containing multiple 96-well plates coated prior to use with 1.5u per well of at least one peptide of the present invention in 100 $\mu l$ pH 9.5 10 mM $NaHCO_3$ buffer. The kit further comprises materials for enzyme detection in separate sealed containers of: (1) normal human serum (as negative control); (2) heat inactivated HTLV-I or HTLV-II seropositive serum (as positive control); (3) normal goat serum; (4) peroxidase labeled-goat antihuman IgG; and (5) a color change indicator of orthophenylenediamine (OPD) and hydrogen peroxide in phosphate citrate buffer. The procedure described in Example 2 is to be followed.

In this test, 96-well plates, precoated with the peptide of the present invention, can be replaced by polystyrene beads, or multiple mini-columns filled with controlled pore size glass beads, or nitrocellulose paper strip precoated with the peptides of the present invention for use as the solid phase immunoadsorbent.

EXAMPLE 8

A second test kit for detecting antibodies using the immunoradiometric assay (IRMA) comprises a compartmented enclosure containing multiple 96-well bendable polyvinylchloride (PVC) plates precoated with at least one peptide according to the present invention at a concentration of 1.5 ug per well of the peptide in 100 ul of pH 9.5 10mM $NaHCO_3$ buffer and materials for radioimmunoassay including: (1) normal human serum (as negative control); (2) heat inactivated, seropositive HTLV-I or HTLV-II serum (as positive control); (3) normal goat serum; and (4) I-125 labeled goat anti human IgG. The procedure described in Example 4 is to be followed.

In this test kit, 96-well PVC plates precoated with the peptides of the present invention can be replaced by polystyrene beads precoated with the peptide of the present invention for use as the solid phase immunoadsorbent.

All publications, including U.S. Patents, as well as all U.S. patent applications referred to in this application are herein incorporated by reference.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What I claim is:

1. A peptide having specific immunoreactivity to antibodies to HTLV-I, HTLV-II, or combinations thereof consisting essentially of the amino acid sequence SPNVSVPSSSSTPLLY.

2. A peptide having specific immunoreactivity to antibodies to HTLV-I, HTLV-II, or combinations thereof consisting essentially of the amino acid sequence KQILSQRSFPLPPPHK.

* * * * *